(12) United States Patent
Kuhman et al.

(10) Patent No.: US 10,247,534 B2
(45) Date of Patent: Apr. 2, 2019

(54) APPARATUS AND METHOD FOR DETERMINING FEEDSCREW AND BARREL WEAR

(71) Applicant: GLYCON CORP., Tecumseh, MI (US)

(72) Inventors: Jeffrey A. Kuhman, Tecumseh, MI (US); Richard T. Harris, Britton, MI (US)

(73) Assignee: GLYCON CORP., Tecumseh, MI (US)

( * ) Notice: Subject to any disclaimer, the term of this patent is extended or adjusted under 35 U.S.C. 154(b) by 173 days.

(21) Appl. No.: 15/427,078

(22) Filed: Feb. 8, 2017

(65) Prior Publication Data

US 2018/0224265 A1     Aug. 9, 2018

(51) Int. Cl.
    *G01B 5/20*       (2006.01)
    *B29C 47/92*      (2006.01)
    *G01N 3/56*       (2006.01)

(52) U.S. Cl.
CPC .............. *G01B 5/204* (2013.01); *B29C 47/92* (2013.01); *G01N 3/56* (2013.01); *B29C 2947/924* (2013.01); *B29C 2947/92123* (2013.01)

(58) Field of Classification Search
CPC .......... G01B 5/204; G01B 5/20; B29C 47/92; B29C 2947/92123; B29C 2947/924; G01N 3/56; G01N 3/567; G01N 2203/0664
USPC .............................................. 33/199 R; 73/7
See application file for complete search history.

(56) References Cited

U.S. PATENT DOCUMENTS

| | | | | |
|---|---|---|---|---|
| 3,849,893 A | * | 11/1974 | Ormsby | .................. G01B 5/14 198/657 |
| 3,932,941 A | * | 1/1976 | Ormsby | .................. G01B 5/14 73/7 |
| 4,604,251 A | | 8/1986 | Kuhman | |
| 5,348,453 A | * | 9/1994 | Baran et al. | ........ B29C 47/0845 417/440 |
| 7,134,316 B2 | | 11/2006 | Kuhman et al. | |
| 7,168,291 B2 | | 1/2007 | Kuhman et al. | |
| 7,409,775 B2 | | 8/2008 | Kuhman et al. | |

FOREIGN PATENT DOCUMENTS

| | | | | |
|---|---|---|---|---|
| JP | 08142160 A | * | 6/1996 | ............. B29C 47/92 |
| JP | 2003311816 A | * | 11/2003 | ............. B29C 47/92 |

* cited by examiner

*Primary Examiner* — R. A. Smith
(74) *Attorney, Agent, or Firm* — William J. Clemens; Shumaker, Loop & Kendrick, LLP (57) ABSTRACT

An assembly for measuring wear of a barrel and feedscrew combination, wherein the barrel has a longitudinally extending feedscrew disposed therein and a radially extending measuring aperture formed in a wall thereof, includes a measuring probe having a proximity detecting sensor, a barrel plug for removable insertion into the measuring aperture, and a measuring fixture. The barrel plug is configured to undergo wear in an axial direction thereof while inserted into the measuring aperture. The measuring probe and the barrel plug are installed into the measuring fixture for determining wear of the barrel plug in the axial direction thereof. The measuring probe is further configured for removable insertion into the measuring aperture for measuring wear of a flight of the feedscrew. A spacer and rotational tool cooperate with the measuring probe when installing the measuring probe in the measuring aperture.

20 Claims, 7 Drawing Sheets

APPARATUS AND METHOD FOR DETERMINING FEEDSCREW AND BARREL WEAR

FIELD OF THE INVENTION

The invention relates generally to an apparatus and method for detecting wear in a material processing machine and, in particular, to an apparatus and method for determining the wear of a feedscrew flight and the wear of an interior surface of a barrel accommodating the feedscrew.

BACKGROUND OF THE INVENTION

Typically, a barrel and feedscrew are used to mix and melt various materials for extrusion, blowmolding, and injection processes. For example, bulk plastic material is fed into an extruder, an injection molding machine, or a blow molder through a barrel or cylinder utilizing a rotating helical screw. Such a machine is operated at an elevated temperature and if it is required to be shut down, the plastic material tends to solidify. Many plastic materials are highly abrasive and tend to wear the flights on the screw thereby widening the gap between the outer edge of the flights and the inner surface of the barrel. Such a condition will tend to prevent the uniform free flow of material through the barrel thereby causing problems in the consistency of the plastic material. Other problems that can occur are galling in the barrel through adhesive wear, metal to metal contact within the barrel, and misalignment of the screw through excessive shear or deflection of the screw mechanism.

Previously, the only way to check the dimensional clearances in such a mechanism was to shut it down and remove the screw from the barrel. Since the plastic material would solidify, the screw and the barrel would have to be cleaned and the dimensions checked utilizing mechanical measuring devices. Then, the mechanism would have to be reassembled. Such a procedure tended to result in lost production time and did not completely eliminate the occasional breakdowns between regular measurements.

In U.S. Pat. No. 4,604,251, there is shown an apparatus and method for checking the dimensional relationship between the screw flights and the inner diameter of a barrel during the operation of the plastic material feed device. Utilizing the Foucault current or eddy method of detection, a probe is located in an aperture formed in the side of the barrel. The end of the probe includes a sensor positioned near the inner surface of the barrel. The probe generates an electrical signal having a magnitude proportional to the distance between the outer edge of the flight on the screw and a sensing coil located in the sensor of the probe. The probe output signal is sensed and converted to a digital distance display for use by the machine operator. The magnitude of the signal can be scaled to generate a display number representing the actual measurement between the edge of the flight screw and the inside of the barrel in English or metric units. The signal can be stored, selectively reset, and two or more probe detection signals can be selectively displayed.

The most time efficient manner of measuring the wear on the screw involves measuring the relevant distances within the barrel during rotation of the screw therein. However, one problem encountered when attempting to measure the distances within the barrel using the aforementioned probe relates to the heat generated by the rotation of the screw within the barrel. The heat generated by use of the screw can potentially damage the sensor of the probe if the sensor is exposed to elevated temperatures within the barrel for an extended period of time. There accordingly exists a need for a method of quickly installing the probe and making the proper measurements prior to the probe undergoing damage as a result of exposure to heat within the barrel.

In U.S. Pat. No. 7,168,291, there is further shown an apparatus and method for checking the amount of wear experienced by the inner surface of the barrel or cylinder in addition to the wear experienced by the flight of the screw. A plug having an inner contour matching that of the inner surface of the barrel or cylinder is placed into the aperture formed in the side of the barrel or cylinder and retained therein by a plug retainer. The plug remains in position during an extended period of use of the screw to cause the inner contour of the plug to undergo wear in a manner consistent with the remainder of the inner surface of the barrel or cylinder. The plug is then removed from the aperture and the degree of wear experienced by the plug is determined by measuring an axial length of the plug and comparing the measured length to the length of the plug prior to placement in the aperture of the barrel or cylinder.

The measurement of the axial length of the plug may require the use of additional measuring devices and fixtures following the removal of the plug from the barrel, thereby further complicating the process of determining the wear experienced by the barrel.

There accordingly exists a need for a method and apparatus suitable for measuring both the wear experienced by the screw and the wear experienced by the barrel or cylinder accommodating the screw in an accurate and time efficient manner while utilizing a reduced number of components. There further exists a need to utilize these measured and recorded values in order to predictively maintain a production installation having the barrel and feedscrew assembly by preventatively avoiding undesirable part damage or failure.

SUMMARY OF THE INVENTION

Concordant and consistent with the present invention, an efficient and timely method of monitoring, measuring, and recording the wear conditions of a production installation utilizing a barrel and feedscrew combination has surprisingly been discovered.

In one embodiment of the invention, an assembly for determining wear of a feedscrew comprises a barrel having a central bore extending along a longitudinal axis and a measuring aperture extending radially from the central bore, the measuring aperture including a first threaded portion, a feedscrew rotatably disposed in the central bore, and a measuring probe configured for removable insertion into the measuring aperture. The measuring probe includes a measuring sensor, a longitudinally extending stem, and a retainer slidably disposed over the stem. The retainer includes a second threaded portion configured to mate with the first threaded portion of the measuring aperture.

According to another aspect of the invention, a method of determining wear of a feedscrew and barrel combination comprises the steps of: providing a barrel, a feedscrew, and a measuring fixture, the barrel having a central bore extending along a longitudinal axis and a measuring aperture extending radially from the central bore, the feedscrew rotatably disposed within the central bore of the barrel, and the measuring fixture including a through aperture extending from a first end to a second end thereof; rotating the feedscrew while a barrel plug is inserted in the measuring aperture, the barrel plug having an inner end with a curvature corresponding to a curvature of an inner surface of the barrel defining the central bore thereof; removing the barrel plug from the measuring aperture following the rotating of the feedscrew; inserting a measuring probe in the first end of the through aperture of the measuring fixture, a first end of the measuring probe in facing relationship with the inner end of the barrel plug; inserting the barrel plug into the second end of the through aperture of the measuring fixture; and measuring a distance between the inner end of the barrel plug and the first end of the measuring probe.

According to yet another aspect of the invention, a method of determining wear of a feedscrew comprises the steps of: providing a barrel and a feedscrew, the barrel having a central bore extending along a longitudinal axis and a measuring aperture extending radially from the central bore, and the feedscrew rotatably disposed within the central bore of the barrel; inserting a measuring probe into the measuring aperture until a sensor disposed at an inner end of the measuring probe is positioned at a reference position; rotating the feedscrew within the central bore; and continuously measuring and recording a distance formed between the sensor of the measuring probe and a portion of the feedscrew facing the measuring aperture during the rotating of the feedscrew.

BRIEF DESCRIPTION OF THE DRAWINGS

The above, as well as other advantages of the present disclosure, will become readily apparent to those skilled in the art from the following detailed description, particularly when considered in the light of the drawings described hereinafter.

DETAILED DESCRIPTION OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical unless noted otherwise.

Figure 1:
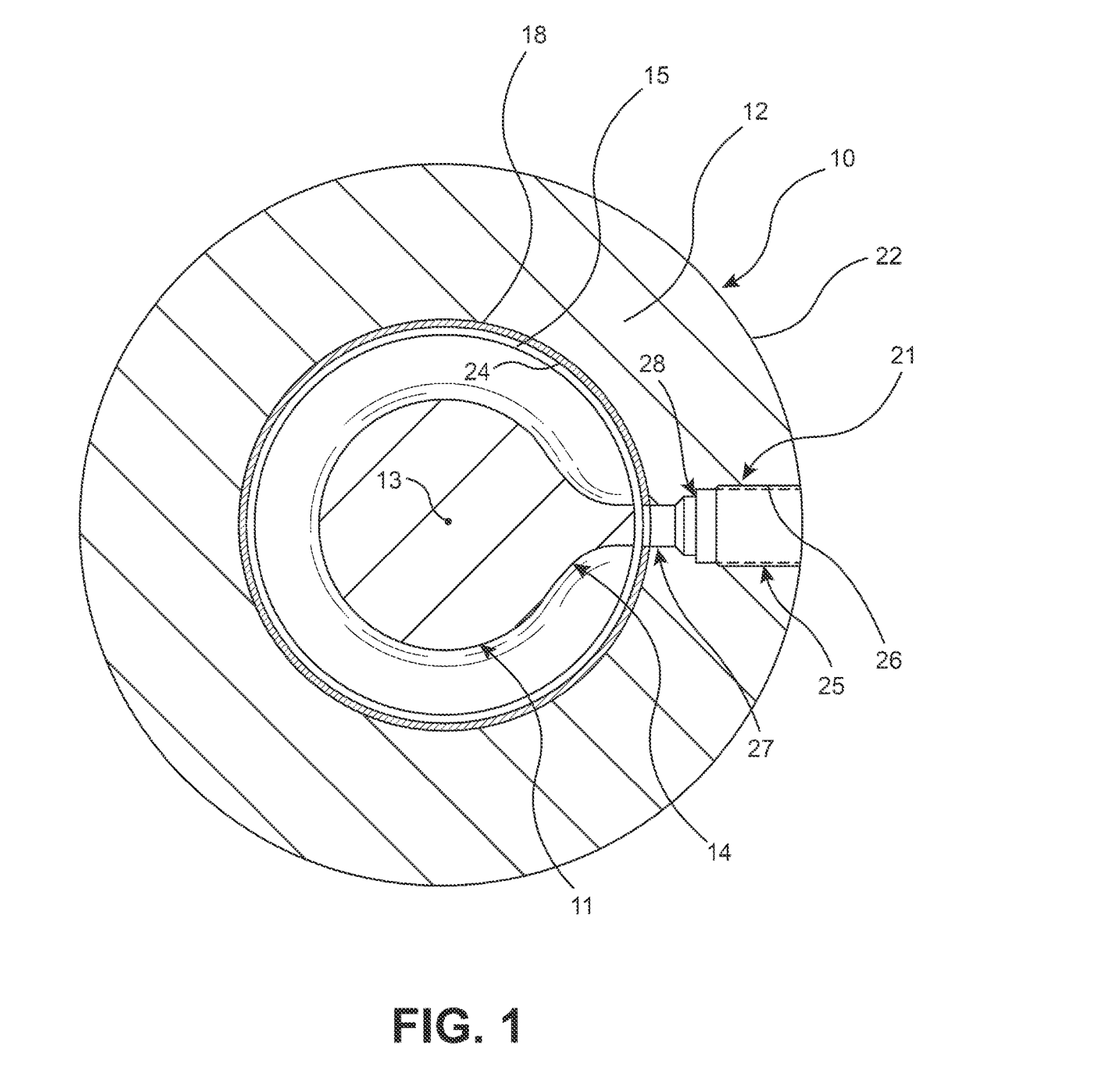
FIG. 1 is an enlarged cross-sectional view of a barrel having a feedscrew and a radially extending measuring aperture according to an embodiment of the invention.

FIG. 1 illustrates a barrel 10 having a feedscrew 11 disposed therein. The barrel 10 includes a circumferentially extending and cylindrically shaped wall 12 having a central bore 15 formed therein in which the feedscrew 11 is positioned for rotation. The feedscrew 11 extends along a longitudinal axis 13 thereof (extending into the plane of the page) as a cylindrical body with a helical flight 14 formed on an exterior thereof. The wall 12 defining the central bore 15 may be covered by a liner or coating 18 used to reduce wear caused by the material passing through the barrel 10. Typically, the liner or coating 18 is formed of a material that is more abrasion resistant than the material from which the remainder of the barrel 10 is formed. The feedscrew 11 and the barrel 10 are of conventional construction and are available from Glycon Corp. of Tecumseh, Mich.

A measuring aperture 21 extends through the wall 12 of the barrel 10 and the liner or coating 18. The aperture 21 extends radially relative to the axis 13 from an outer surface 22 of the barrel 10 to an inner surface 24 of the liner or coating 18. Extending inwardly from the outer surface 22, the aperture 21 has a larger diameter portion 25 that includes an internally threaded portion 26. Extending outwardly from the inner surface 24, the aperture 21 has a smaller diameter portion 27 that joins the larger diameter portion 25 at a step 28.

Figure 2:
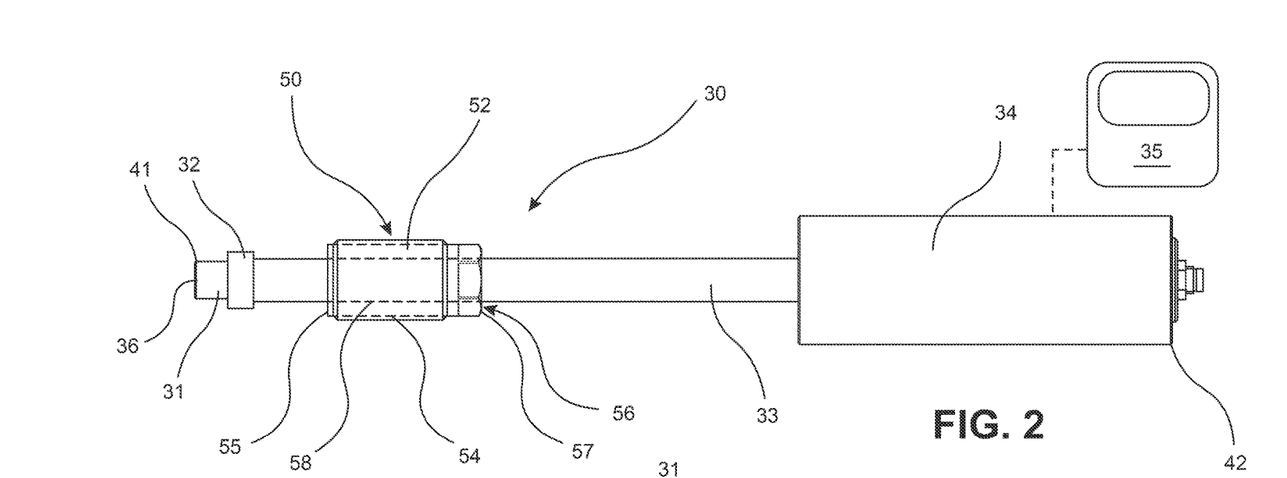
FIG. 2 is a side elevational view of a measuring probe for insertion into the measuring aperture of the barrel illustrated in FIG. 1.
Figure 3:
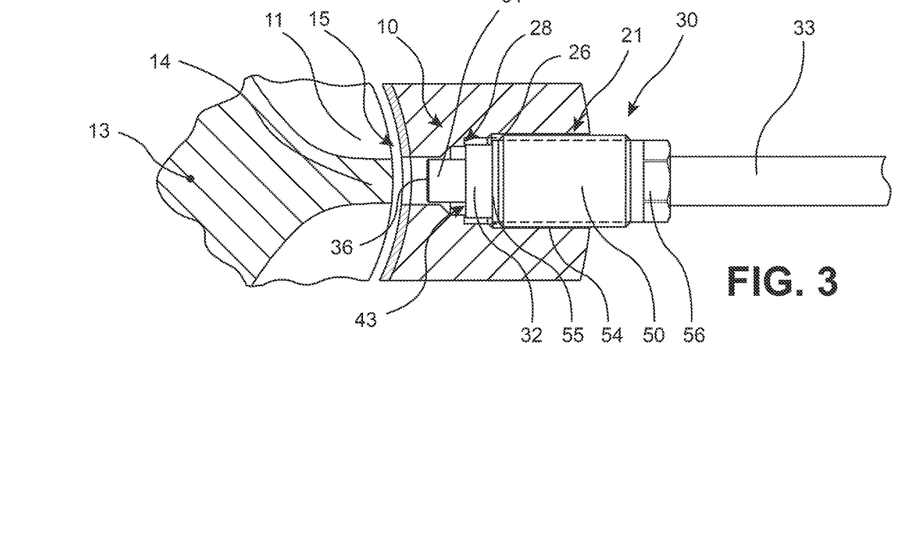
FIG. 3 is a fragmentary partial cross-sectional view showing the measuring probe of FIG. 2 when fully inserted into the measuring aperture of the barrel of FIG. 1.

The measuring aperture 21 is configured to receive a probe 30 therein for measuring the wear of the feedscrew 11. As shown in FIGS. 2 and 3, the probe 30 includes a smaller diameter portion 31 formed at a first end thereof 41, a larger diameter portion 32 formed adjacent the smaller diameter portion 31, a component housing 34 formed at a second end 42 thereof, and a stem 33 extending between the larger diameter portion 32 and the component housing 34. A shoulder 43 is formed on the probe 30 at the intersection of the smaller diameter portion 31 and the larger diameter portion 32 for engaging the step 28 of the aperture 21.

A sensor 36 is disposed at an end of the smaller diameter portion 31 opposite the larger diameter portion 32. An electrical connection (not shown) may extend from the sensor 36 to at least one associated electrical component (not shown) disposed within the component housing 34. The electrical connection may carry power to the sensor 36 and may additionally carry signals from the sensor 36 to the associated computational component configured to collect and analyze the signals retrieved from the sensor 36. The electrical connection may extend through each of the smaller diameter portion 31, the larger diameter portion 32, the stem 33, and at least a portion of the component housing 34, for example.

The sensor 36 of the probe 30 can use any known type of proximity detection technology. The sensor 36 may for example utilize a Foucault current or eddy method of detection wherein the sensor 36 generates an electrical signal having a magnitude proportional to a distance present between a sensing coil located in the sensor 36 and a desired surface spaced from the sensor 36. This signal may in turn be analyzed and converted to a corresponding distance measurement value. Other proximity detection technology may also be used without departing from the scope of the present invention.

The signals generated by the sensor 36 may be communicated to a display unit 35 in signal communication with the sensor 36. The display unit 35 may be in direct signal communication with the sensor 36 through the electrical connection or the display unit 35 may be in indirect signal communication with the sensor 36 via an associated electrical component disposed within the component housing 34, as a non-limiting example. The display unit 35 may be in wireless signal communication with the sensor 36 or the electrical component associated with the sensor 36.

The display unit 35 is configured to receive, record, and analyze the signals generated by the sensor 36 in order to generate and display data relevant to the operation of the probe 30 to a user of the probe. For example, the signals received from the sensor 36 may be analyzed and converted to a corresponding distance value for visual display on the display unit 35. The display unit 35 may additionally have smart device capabilities allowing for the display unit 35 to further communicate the received signals or outputted data to additional electrical or computational components in signal communication with the display unit 35, as desired.

The display unit 35 may for example be a Hocking "Locator 2" handheld eddy current inspection unit or a Hocking "Phasec 2" eddy current inspection unit, both available from GE Inspection Technologies, LP of Lewistown, Pa., or the display unit 35 may be in signal communication with such a device.

The probe 30 further includes a probe retainer 50 slidably disposed over the stem 33 of the probe 30 for properly positioning and retaining the probe 30 in the aperture 21 of the barrel wall 12. The probe retainer 50 includes a cylindrical body 52 extending from a first end 55 to a second end 57 thereof. A through aperture 58 is formed along a central longitudinal axis of the cylindrical body 52 and extends from the first end 55 to the second end 57 thereof. The through aperture 58 includes an inner diameter greater than that of the stem 33 of the probe 30 to allow the probe retainer 50 to be capable of axial movement relative to the stem 33. An externally threaded portion 54 is formed on the cylindrical body 52 adjacent the first end 55 of the probe retainer 50. The cylindrical body 52 further includes a tool engagement portion 56 formed at the second end 57 thereof. The tool engagement portion 56 may include a hexagonal shaped outer surface sized for a standard socket wrench (not shown) of suitable size for rotating the probe retainer 50.

With reference to FIG. 3, the probe 30 is used for measuring the wear of the feedscrew 11 as follows. The sensor 36 of the probe 30 is inserted into the measuring aperture 21 until the shoulder 43 abuts the step 28 of the measuring aperture 21. The probe retainer 30 is then moved axially relative to the stem 33 of the probe 30 until the externally threaded portion 54 of the probe retainer 50 engages the internally threaded portion 26 of the measuring aperture 21. The probe retainer 50 is then rotated relative to the measuring aperture 21 until the first end 55 of the probe retainer 50 abuts the larger diameter portion 32 of the probe 30. The rotation of the probe retainer 50 may be accomplished using a corresponding wrench or similar tool configured to engage the tool engagement portion 56 of the probe retainer 50.

Once the probe retainer 50 is fully installed into the measuring aperture 21, the probe 30 is constrained in position relative to the barrel 10. A distance between the axis 13 of the feedscrew 11 and the step 28 of the measuring aperture 21 in an axial direction thereof is known as is a distance between the shoulder 43 and the sensor 36 of the probe 30.

The feedscrew 11 is then caused to rotate within the central bore 15 to cause the helical flight 14 to periodically pass by the measuring aperture 21. The probe 30 is then activated to cause the sensor 36 to continuously generate signals corresponding to a measurement of a distance present between the sensor 36 and the instantaneous nearest portion of the feedscrew 11 passing by the measuring aperture 21 during rotation of the feedscrew 11. The generated signals are then communicated to the display unit 35 to be recorded and analyzed.

During periods of time when the flight 14 is facing away from the measuring aperture 21, the sensor 36 measures a maximized distance. In contrast, when the flight 14 is pointed directly towards the measuring aperture 21, a minimized distance is measured. The sensor 36 may further measure and record intermediate distances between the maximized and the minimized distances as the flight 14 approaches and passes by the measuring aperture 21, as desired, for determining the wear of any portion of the circumference of the feedscrew 11 in axial alignment with the measuring aperture 21.

The feedscrew 11 may be rotated through a plurality of revolutions to result in a plurality of maximized measured distances and a plurality of minimized measured distances communicated to the display unit 35. Using these recorded measurements and the known relationships between the probe 30 and the barrel 10, the distance between the axis 13 of the feedscrew 11 and any given portion of an outer surface of the feedscrew 11 may be calculated by the display unit 35 using the signals received from the sensor 36 for each revolution of the feedscrew 11. The maximum calculated distance measured during each revolution of the feedscrew 11 corresponds to the portion of the feedscrew 11 having a minimized diameter (a portion of the feedscrew 11 formed in the absence of the flight 14) while the minimum distance measured during each revolution corresponds to the distal end of the flight 14 having the maximized distance from the axis 13 of the feedscrew 11. The distance calculated between the axis 13 of the feedscrew 11 and the given portion of the outer surface thereof is then used to determine if the feedscrew 11 has worn along any given portion thereof by comparison of the measured distance to the known dimensions of the feedscrew 11 in the absence of wear. For example, a measured distance between the axis 13 of the feedscrew 11 and the distal end of the flight 14 during rotation of the feedscrew 11 as determined by the sensor 36 and the display unit 35 may be compared to a known distance formed between the flight 14 and the axis 13 of the feedscrew 11 prior to use of the feedscrew 11, as stored to the display unit 35, to determine if the feedscrew 11 has experienced wear.

During the rotation of the feedscrew 11 within the barrel 10, it may be common for the sensor 36 to measure various different maximized and minimized distances for the same portion of the circumference of the feedscrew 11 due to slight movements of the axis 13 of the feedscrew 11 during rotation thereof, also referred to as the procession of the feedscrew 11 within the barrel 10. In order to account for these variations, each of the plurality of the minimized measured distance values and each of the plurality of the maximized measured distance values recorded by the display unit 35 during the plurality of revolutions of the feedscrew 11 may be averaged together to determine an average minimum distance value and an average maximum distance value. Using these averaged values, the true degree of wear on the feedscrew 11 may be more accurately determined by accounting for the variations in the position of the axis 13 of the feedscrew 11 relative to the sensor 36 of the probe 30 during active use of the feedscrew 11. Additionally, the measured maximum and minimum values may further be used to determine the degree of procession experienced by the feedscrew 11, wherein large variations in the measured distances for a specific portion of the feedscrew 11 indicate a high degree of procession and small variations in the measured distances for a specific portion of the feedscrew 11 indicate a low degree of procession. The display unit 35 may accordingly be configured to determine and display these averaged values in accordance with the method described hereinabove.

The electrical components associated with the sensor 36 may be subject to damage or failure when subjected to the temperatures present within the barrel 10, and especially during rotation of the feedscrew 11 within the barrel 10 during the measuring process described hereinabove. For example, the electrical components of the sensor 36 may be subject to failure at temperatures above 500° F. or potential damage during extended exposure to temperatures above 350° F. Accordingly, FIGS. 4-8 illustrate a split collar spacer 60 and a rotational tool 70 configured for minimizing the time needed to properly install the probe 30 into the measuring aperture 21 to minimize the time period in which the sensor 36 is exposed to the elevated temperatures within the barrel 10.

Figure 4:
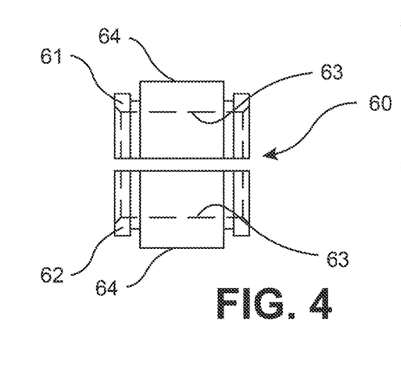
FIG. 4 is a side elevational view of a split collar spacer according to one aspect of the invention.
Figures 5, 6:
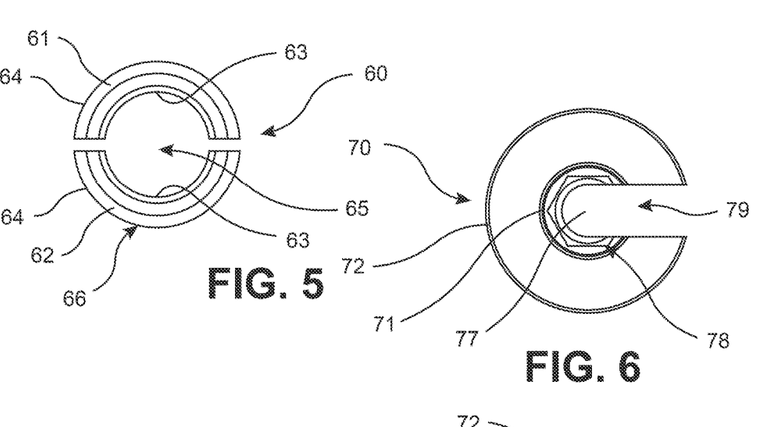
FIG. 5 is a front elevational view of the split collar spacer of FIG. 4.
FIG. 6 is a front elevational view of a rotational tool according to one aspect of the invention.

As shown in FIGS. 4 and 5, the split collar spacer 60 comprises a first collar portion 61 and a second collar portion 62. The first collar portion 61 and the second collar portion 62 each include a substantially semi-circular inner surface 63 and a substantially semi-circular outer surface 64. When the first collar portion 61 is brought into engagement with the second collar portion 62, the semi-circular inner surfaces 63 thereof cooperate to form a substantially cylindrical through aperture 65 and the semi-circular outer surfaces 64 thereof cooperate to form a substantially cylindrical outer circumferential surface 66. The through aperture 65 has an inner diameter configured to receive the stem 33 of the probe 30 therein. The outer circumferential surface 66 is sized to be axially received within the measuring aperture 21 of the barrel 10.

Figure 7:
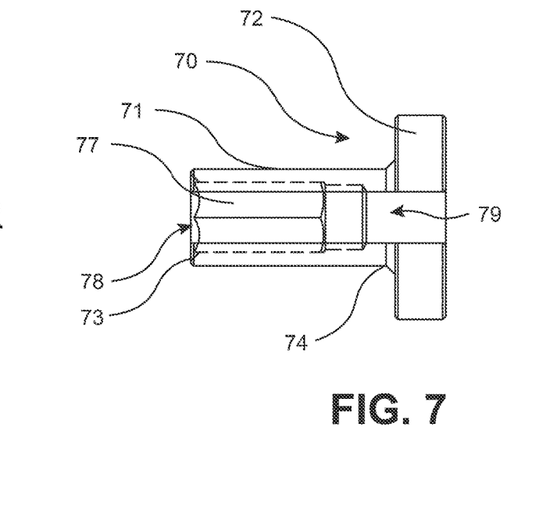
FIG. 7 is a side elevational view of the rotational tool of FIG. 6.

As shown in FIGS. 6 and 7, the rotational tool 70 extends includes a cylindrical body 71 and a radially outwardly extending and cylindrical flanged portion 72. The cylindrical body 71 extends from a first end 73 to a second end 74 thereof. The flanged portion 72 is disposed at the second end 74 of the cylindrical body 71 and has an outer diameter that is greater than an outer diameter of the cylindrical body 71. A through aperture 77 extends in an axial direction of the rotational tool 70 and extends through each of the cylindrical body 71 and the flanged portion 72. The through aperture 77 may have a diameter substantially equal to or slightly larger than the outer diameter of the stem 33 of the probe 30. The through aperture 77 expands to form a retainer opening 78 at the first end 73 of the cylindrical body 71. The retainer opening 78 has a hexagonal cross-sectional shape configured to mate with the hexagonal outer surface of the tool engagement portion 56 of the probe retainer 50. The rotational tool 70 further includes a side opening 79 formed therein. The side opening 79 extends radially outwardly from the through aperture 77 to an outer surface of each of the cylindrical body 71 and the flanged portion 72. The side opening 79 has a width substantially equal to each of the through aperture 77 and the stem 33 of the probe 30 to allow the stem 33 to be received within the side opening 79 when the probe 30 and the rotational tool 70 are moved laterally relative to each other.

Figure 8:
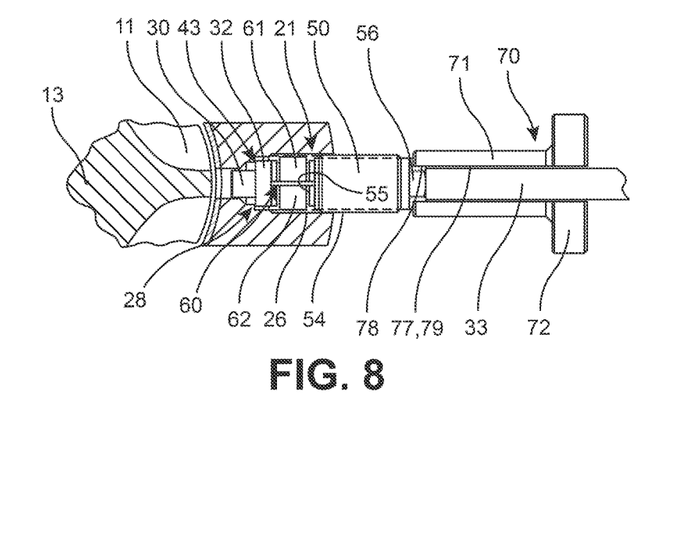
FIG. 8 is a fragmentary partial cross-sectional view illustrating a method of use of the split collar spacer of FIGS. 4 and 5 and the rotational tool of FIGS. 6 and 7.

In use, the first collar portion 61 and the second collar portion 62 of the split collar spacer 60 are brought into engagement with each other between the larger diameter portion 32 of the probe 30 and the probe retainer 50 while straddling the stem 33 of the probe 30, as shown in FIG. 8. The probe 30 is inserted into the measuring aperture 21 in an axial direction thereof until the shoulder 43 of the probe 30 abuts the step 28 of the measuring aperture 21 with the split collar spacer 60 still in contact with the larger diameter portion 32 of the probe 30. After positioning the split collar spacer 60 and the probe 30 within the measuring aperture 21, the threaded portion 54 of the probe retainer 50 engages the threaded portion 26 of the measuring aperture 21. The probe retainer 50 may then be rotated to cause the larger diameter portion 32 and the split collar spacer 60 to be sandwiched between the step 28 and the first end 55 of the probe retainer 50.

As best shown in FIG. 8, the split collar spacer 60 extends longitudinally along at least a portion of the threaded portion 26 of the measuring aperture 21 when placed within the measuring aperture 21. As such, the split collar spacer 60 aids in more quickly installing the probe 30 into the measuring aperture 21 by requiring a smaller portion of the threaded portion 26 of the measuring aperture 21 to be traversed by the threaded portion 54 of the probe retainer 50 when the probe retainer 50 is used to secure the probe 30 within the measuring aperture 21. The shortened exposed threaded portion 26 causes the probe retainer 50 to require fewer turns to sandwich the split collar spacer 60 and the larger diameter portion 32 of the probe 30 between the probe retainer 50 and the step 28 of the measuring aperture 21, which reduces a period of time it takes to properly position the probe 30 for measuring the distances within the barrel 10. This reduction in time accordingly prevents the incidence of heat damage to the sensor 36 caused by extended exposure to elevated temperatures within the measuring aperture 21.

The rotational tool 70 further aids in installing the probe 30 into the measuring aperture 21 more quickly to avoid exposure of the probe 30 to heat within the barrel 10. The rotational tool 70 is placed over the stem 33 of the probe 30 by lateral movement of the side opening 79 and the through aperture 77 relative to the stem 33, as shown in FIG. 8. The rotational tool 70 is then moved axially to cause engagement of the tool engagement portion 56 of the probe retainer 50 with the retainer opening 78 of the rotational tool 70. The flanged portion 72 of the rotational tool 70 is then grasped by a user and rotated to cause rotation of the threaded portion 54 of the probe retainer 50 relative to the threaded portion 26 of the measuring aperture 21. The increased diameter of the flanged portion 72 aids in more easily and quickly installing and removing the probe retainer 50 by lessening the force required to rotate the probe retainer 50, thereby further reducing a period of time required to install the probe 30 into the measuring aperture 21. The rotational tool 70 therefore similarly reduces the incidence of heat damage to the sensor 36.

The split collar spacer 60 may be selected to have a desired length based on a length of the measuring aperture 21 and/or the threaded portion 26 thereof. The length of the split collar spacer 60 may be selected to expose a minimized suitable length of the threaded portion 26 of the measuring aperture 21 to ensure the probe 30 is installed as quickly as possible while being suitably retained within the measuring aperture 21.

The probe 30 may also be used in conjunction with a barrel plug 110 for determining wear experienced by the wall 12 defining the central bore 15, and more specifically to determine the wear experienced by the liner or coating 18 disposed on the interior surface of the wall 12 of the barrel 10. Accordingly, the probe 30 may be used to aid in determining the wear on each of the wall 12 of the barrel 10 and any specified portion of the feedscrew 11, as explained in greater detail hereinafter.

Figures 9, 10, 11:
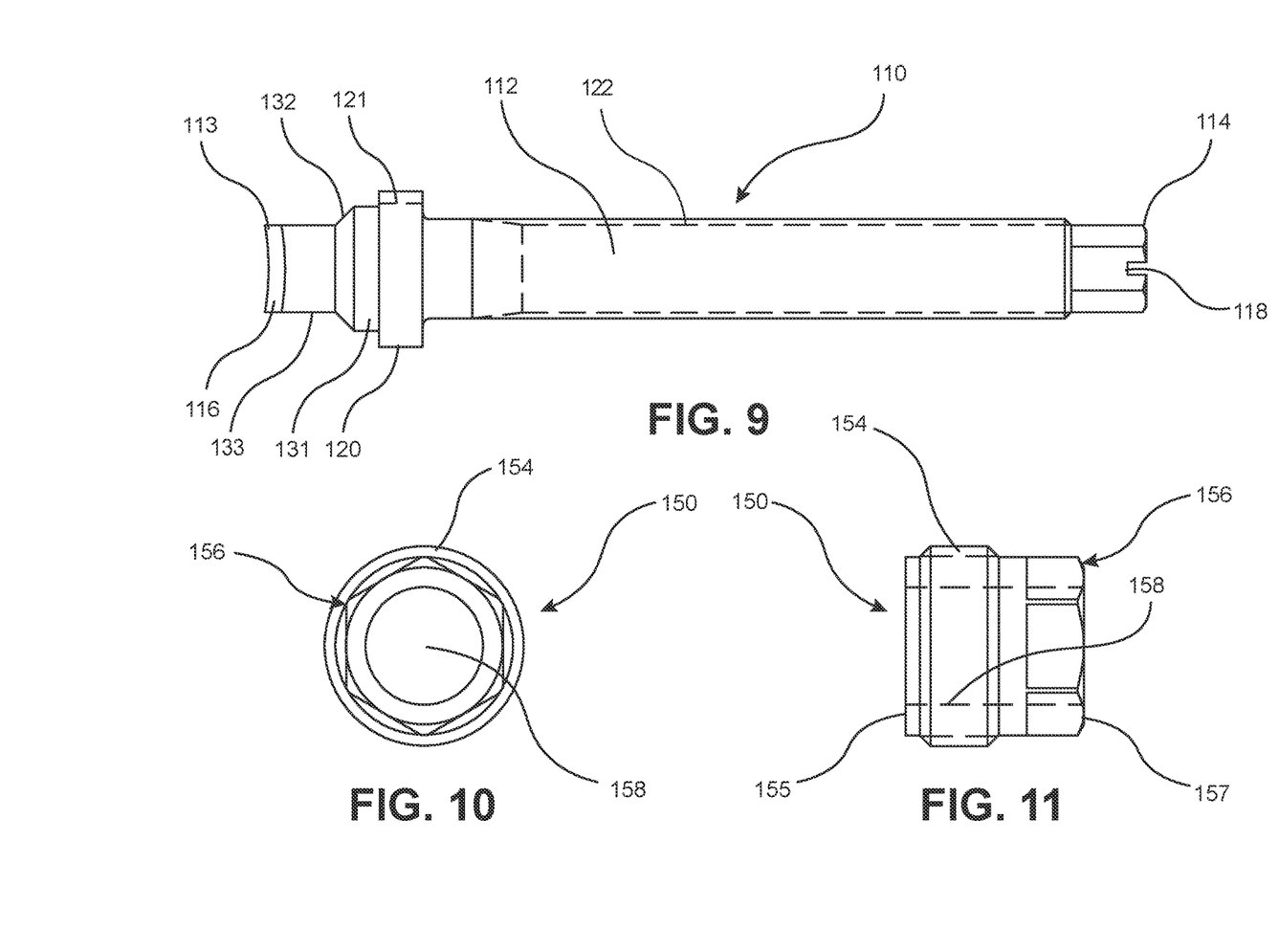
FIG. 9 is a side elevational view of a barrel plug according to one aspect of the invention.
FIG. 10 is a front elevational view of a plug retainer for use with the barrel plug of FIG. 9.
FIG. 11 is a side elevational view of the plug retainer of FIG. 10.

As shown in FIG. 9, the barrel plug 110 includes a cylindrical body 112 extending from a first end 113 to a second end 114 thereof. The first end 113 of the body 112 includes a cap 116 having an outwardly facing surface that is curved to correspond to the curvature of the barrel wall 12 including the optional lining or coating 18. The cap 116 may be formed from the same material forming the liner or coating 18 of the barrel 10. Alternatively, the body 112 may be devoid of the cap 116 if the entirety of the body 112 is formed from the same material as the liner 18 of the wall 12 or from a material having similar wear characteristics to the liner 18 of the wall 12. In either event, it is understood that the first end 113 of the body is intended to have the same wear characteristics as the innermost surface of the wall 12 defining the bore 15 to allow the barrel plug 110 to experience wear at the same rate as the remainder of the barrel 10.

A recess 118 is formed in the second end 114 of the body 112. The recess 118 may be configured to receive a tool (not shown) to aid in positioning the barrel plug 110 in the aperture 21.

Figure 12:
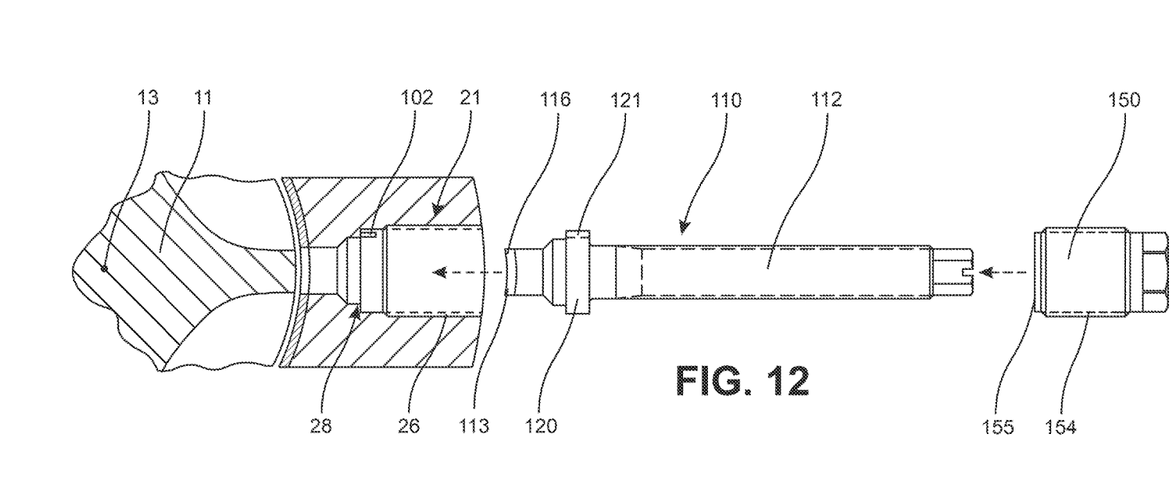
FIG. 12 is a fragmentary partial cross-sectional view showing a method of installing the barrel plug and plug retainer of FIGS. 9-11 into a measuring aperture.

The body 112 includes a radially extending flange 120 adjacent the first end 113 thereof. The flange 120 has a peripheral groove 121 extending parallel to the axis of the aperture 21. The measuring aperture 21 is shown in FIG. 12 as including a pin or dowel 102 mounted in the barrel wall 12 and extending parallel to an axis of the aperture 21. The peripheral groove 121 is configured for receiving the dowel 102 to align the curved first end 113 of the barrel plug 110 to correspond to the curvature of the inner surface of the barrel 10. An externally threaded portion 122 of the body 112 is positioned between the second end 114 and the flange 120. The threaded portion 122 is configured to mate with a tool (not shown) used to aid in removing the barrel plug 110 from the measuring aperture 21.

The body 112 of the barrel plug 110 further includes a plug outer section 131, a plug intermediate section 132, and a plug inner section 133 formed between the flange 120 and the cap 116. The sections 131, 132, 133 are shaped and sized to substantially correspond to a shape and size of the smaller diameter portion 27 of the measuring aperture 21. The portion of the body 112 formed intermediate the second end 114 and the flange 120 may have an outer diameter substantially equal to or smaller than the diameter of the measuring aperture 21.

The barrel plug 110 may be used in conjunction with a plug retainer 150 for securing the barrel plug 110 within the measuring aperture 21. As shown in FIGS. 10 and 11, the plug retainer 150 includes a through aperture 158 extending through a central longitudinal axis of the plug retainer 150 from a first end 155 to a second end 157 thereof. An externally threaded portion 154 begins adjacent the first end 155 and extends along a portion of a length of the plug retainer 150. The second end 157 includes a tool engagement portion 156 having a hexagonal shaped outer surface suitable for mating with a corresponding socket or similar tool, as desired. The tool engagement portion 156 may for example have the same structural configuration as the tool engagement portion 56 of the probe retainer 50.

Figure 13:
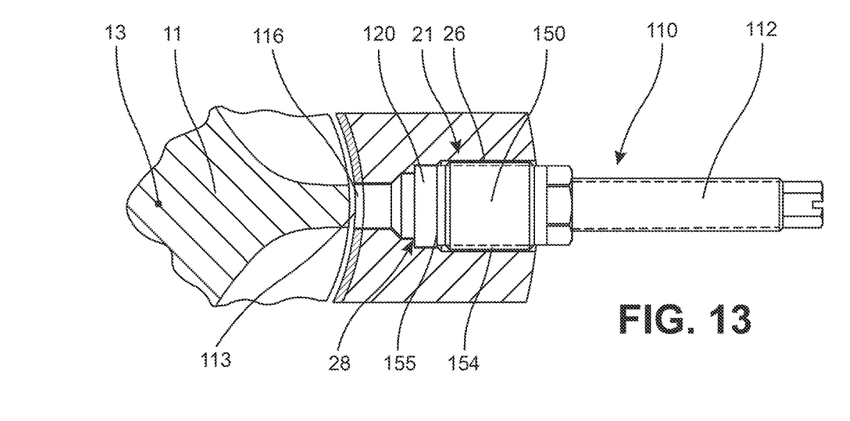
FIG. 13 is a fragmentary partial cross-sectional view showing the barrel plug and the plug retainer when installed into the measuring aperture.

As shown in FIGS. 12 and 13, the barrel plug 110 is axially extended into the measuring aperture 21 until the flange 120 abuts the step 28 of the measuring aperture 21. The barrel plug 110 may require rotation when inserted into the measuring aperture 21 to align the dowel 102 with the groove 121 formed in the flange 120 to allow the flange 120 to come into contact with the step 28 of the measuring aperture 21. Next, the plug retainer 150 is installed over the body 112 in an axial direction until the threaded portion 154 of the plug retainer 150 engages the threaded portion 26 of the measuring aperture 21. The plug retainer 150 is rotated relative to the measuring aperture 21 to cause the plug retainer 150 to move in a direction towards the feedscrew 11 to sandwich the flange 120 of the barrel plug 110 between the step 28 of the measuring aperture 21 and the first end 155 of the plug retainer 150.

Once positioned and retained by the plug retainer 150, the barrel plug 110 is maintained within the measuring aperture 21 during extended rotation of the feedscrew 11 within the barrel 10. The use of the feedscrew 11 may eventually cause the first end 113 of the body 112 to be worn away. Accordingly, following extended use of the feedscrew 11 while the barrel plug 110 is fully installed, the barrel plug 110 may be removed to estimate the degree of wear experienced by the liner 18 of the barrel wall 12 by comparison to the wear experienced by the first end 113 of the body 112 of the barrel plug 110.

Figure 14:
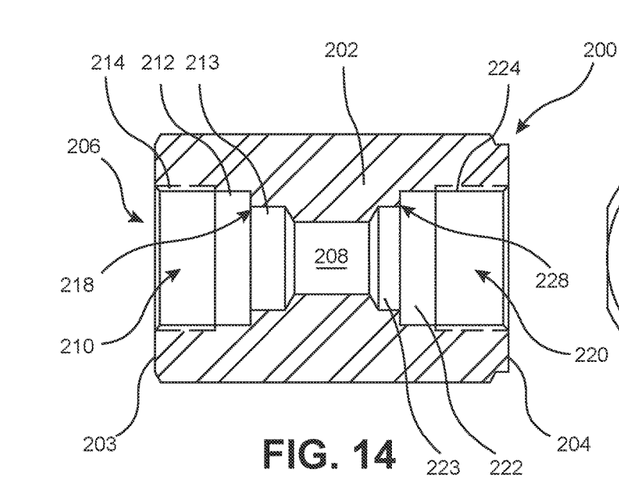
FIG. 14 is a elevational cross-sectional view showing a measuring fixture according to one aspect of the invention.
Figures 15, 17:
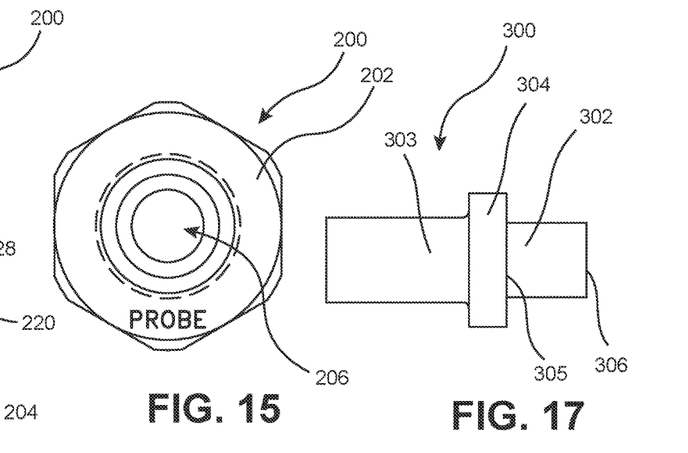
FIG. 15 is a front elevational view of the measuring fixture of FIG. 14.
FIG. 17 is a side elevational view of a calibration plug for use with the measuring fixture of FIGS. 14 and 15.

FIGS. 14 and 15 illustrate a plug measuring fixture 200 for use with each of the probe 30 and the barrel plug 110. The plug measuring fixture 200 includes a substantially cylindrical body 202 having a through aperture 206 extending from a first end 203 to a second end 204 of the body 202. The through aperture 206 includes a plug receiving portion 210 formed at the first end 203 of the body 202 and a probe receiving portion 220 formed at the second end 204 of the body 202. Proceeding from the first end 203 of the body 202 and towards the second end 204 thereof, the plug receiving portion 210 includes a larger diameter portion 212 and a smaller diameter portion 213. The larger diameter portion 212 includes an inner diameter large enough to receive the flange 120 of the barrel plug 110 therein. The smaller diameter portion 213 includes an inner diameter smaller than the outer diameter of the flange 120 and larger than an outer diameter of the cap 116 at the first end 113 of the body 112 of the barrel plug 110. The larger diameter portion 212 intersects the smaller diameter portion 213 at a step 218. The larger diameter portion 212 of the plug receiving portion 210 includes an internally threaded portion 214 extending in an axial direction of the through aperture 206. Proceeding from the second end 204 of the body 202 and towards the first end 203 thereof the probe receiving portion 220 includes a larger diameter portion 222 and a smaller diameter portion 223. The larger diameter portion 222 includes an inner diameter large enough to receive the larger diameter portion 32 of the probe 30 therein. The smaller diameter portion 223 includes an inner diameter smaller than the outer diameter of the larger diameter portion 32 of the probe 30 and larger than an outer diameter of the sensor 36. The larger diameter portion 222 intersects the smaller diameter portion 223 at a step 228. The larger diameter portion 222 of the probe receiving portion 220 includes an internally threaded portion 224 extending in the axial direction of the through aperture 206. A measuring portion 208 of the through aperture 206 is disposed intermediate the smaller diameter portion 213 of the plug receiving portion 210 and the smaller diameter portion 223 of the probe receiving portion 220. The measuring portion 208 is shown as having a reduced diameter in comparison to the smaller diameter portions 213, 223, but the measuring portion 208 may have any diameter, as desired.

As shown in FIG. 15, the ends 203, 204 of the body 202 may be inscribed or otherwise marked with indicia indicating the plug receiving portion 210 and the probe receiving portion 220 of the through aperture 206, as desired.

Figure 16:
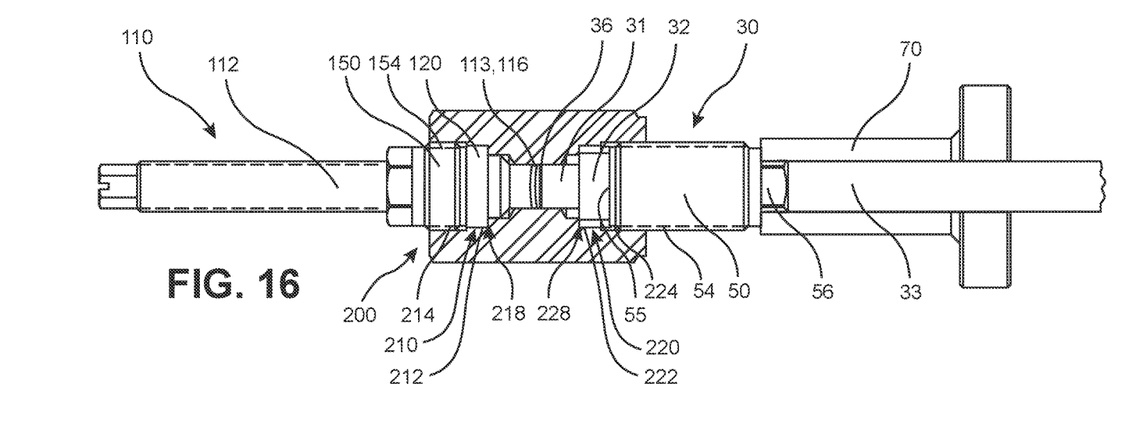
FIG. 16 is a fragmentary partial cross-sectional view showing the measuring fixture of FIGS. 14 and 15 having a measuring probe and a barrel plug inserted therein.

The wear on the barrel plug 110 is determined using both the plug measuring fixture 200 and the probe 30. As shown in FIG. 16, the probe 30 is inserted into the probe receiving portion 220 in an axial direction until the larger diameter portion 32 of the probe 30 abuts the step 228. Next, the probe retainer 50 is slid axially to cause the threaded portion 54 of the probe retainer 50 to engage the threaded portion 224 of the larger diameter portion 222. The probe retainer 50 is then rotated to cause the first end 55 of the probe retainer 50 to sandwich the larger diameter portion 32 of the probe 30 between the step 228 and the probe retainer 50. The probe retainer 50 may be rotated through use of the rotational tool 70 in similar fashion to that described with reference to the measuring aperture 21 of the barrel 10, as desired.

Again referring to FIG. 16, the barrel plug 110 is then inserted into the plug receiving portion 210 until the flange 120 of the barrel plug 110 abuts the step 218. Next, the plug retainer 150 is received over the barrel plug 110 and is slid in an axial direction thereof until the threaded portion 154 of the plug retainer 150 engages the threaded portion 214 of the plug receiving portion 210. The plug retainer 150 is then rotated to sandwich the flange 120 of the barrel plug 110 between the step 218 and the plug retainer 150. Although not pictured, the rotational tool 70 may be utilized to rotate the plug retainer 150 in similar fashion to the probe retainer 50.

Once the probe 30 and the barrel plug 110 are properly positioned within the plug measuring fixture 200, the sensor 36 of the probe 30 is activated to measure a distance between the sensor 36 and a central region of the first end 113 of the barrel plug 110 aligned with the axis of the probe 30. The measured distance may then be communicated to the display unit 35 for further analysis and recordation. The display unit 35 may then be configured to compare the measured distance to a reference distance to determine if the cap 116 has been worn during use of the feedscrew 11.

The reference distance may be determined using a calibration plug 300, which is illustrated in FIG. 17. The calibration plug 300 includes a smaller diameter portion 302, a larger diameter portion 304, and a stem 303. The larger diameter portion 304 is sized to be received within the plug receiving portion 210 of the plug measuring fixture 200 in an axial direction thereof until the larger diameter portion 304 abuts the step 218 of the plug receiving portion 210. The smaller diameter portion 302 has a known length in an axial direction thereof extending from a first end 305 to a second end 306 thereof. The known length of the smaller diameter portion 302 may be established to be equal to a distance formed between the flanged portion 120 of the barrel plug 110 and a center of the cap 116 aligned with a longitudinal axis of the barrel plug 110 prior to the cap 116 being exposed to wear within the barrel 10. For example, the distance formed between the flanged portion 120 and the center of the cap 116 and the length of the smaller diameter portion 302 may each be selected to be the same value of 0.468 inches.

In use, the calibration plug 300 is inserted into the plug receiving portion 210 of the plug measuring fixture 200 in the same manner as the barrel plug 110. The plug retainer 150 is used to secure the position of the calibration plug 300 relative to the plug measuring fixture 200. The probe 30 is inserted into and secured within the probe receiving portion 220 of the plug measuring fixture 200 in the same manner as described hereinabove. The sensor 36 is then activated to measure a distance formed between the second end 306 of the smaller diameter portion 302 of the calibration plug 300 and the sensor 36. This measured distance is communicated to the display unit 35 and establishes the reference distance for calculating the wear of the first end 113 of the body 112 of the barrel plug 110.

After having established and stored this reference distance, the barrel plug 110 is then inserted into the plug measuring fixture 200 in place of the calibration plug 300. The sensor 36 is then activated to measure and record the distance formed between the sensor 36 and the center of the first end 113 of the body 112 in alignment with the sensor 36. If, for example, the smaller diameter portion 302 of the calibration plug 300 is selected to be equal in length to the distance formed between the flanged portion 120 and the center of the first end 113, the difference between the reference distance and the measured distance establishes a distance corresponding directly to the amount of wear experienced by the first end 113 of the body 112. If the smaller diameter portion 302 of the calibration plug 300 is selected to have a different length than the distance formed between the flanged portion 120 and the first end 113, then this difference may also have to be accounted for when determining the amount of wear experienced by the first end 113. The display unit 35 may accordingly be configured to store each required measurement and to then carry out the necessary comparisons and calculations in order to determine and display the amount of wear experienced by the barrel plug 110 to the user of the display unit 35, as desired.

Figure 18:
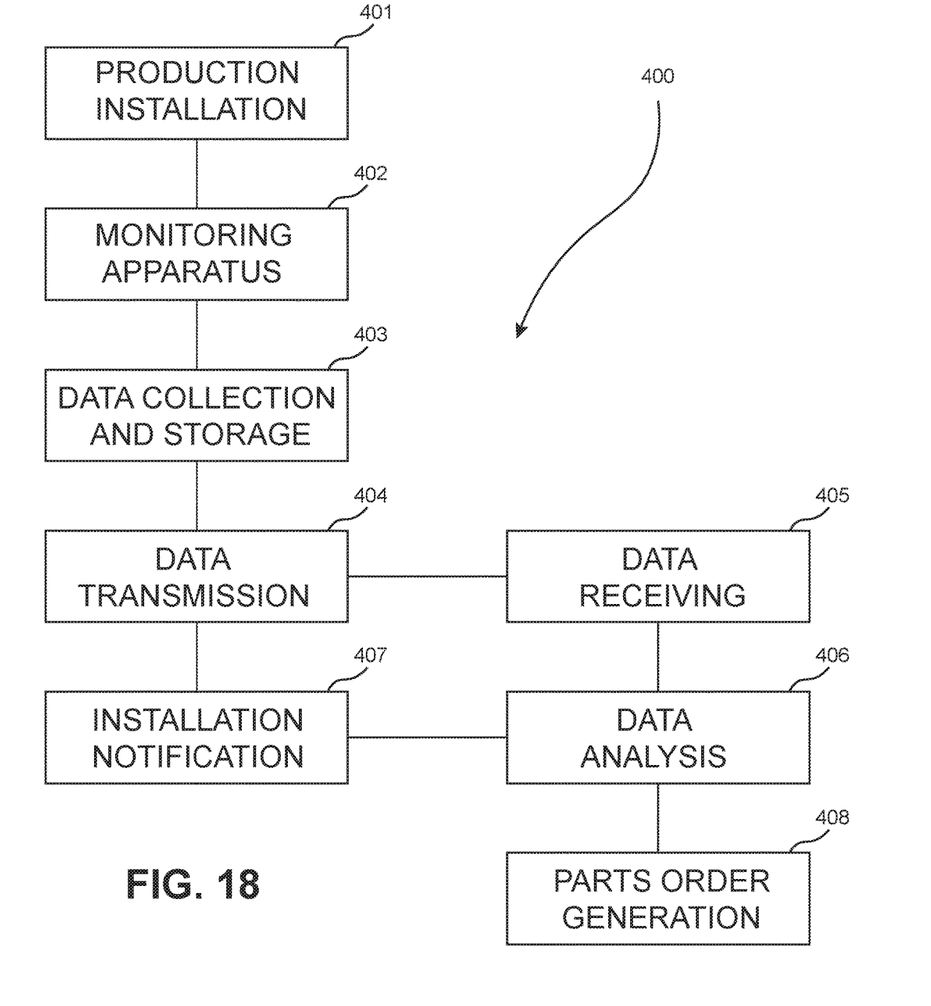
FIG. 18 is a block diagram of a preventative maintenance system for performing a method according to the present invention for monitoring and maintaining production installations.

The probe 30, the barrel plug 110, the plug measuring fixture 200, and the display unit 35 may be used as part of a predictive maintenance system 400 for predicting the failure of the barrel 10, the feedscrew 11, and any related or intervening components. The predictive maintenance system 400 is used to monitor a production installation 401 that may include a single barrel 10 having a single feedscrew 11 or a plurality of barrels and a plurality of feedscrews associated with the plurality of barrels, as desired.

The predictive maintenance system 400, as shown in FIG. 18, comprises a monitoring apparatus 402 such as the probe 30 or the barrel plug 110, as non-limiting examples. The monitoring apparatus 402 provides wear data and related information to a data collection and storage means 403. The related information can include such data as the material being processed, the speed of rotation of the feedscrew 11 and the temperatures being generated in the barrel 10. The stored data can be transmitted by a data transmission means 404 to a central data receiving means 405. A computer program can be provided in a data analysis means 406 for use with the wear detectors according to the present invention. The program can calculate, graph and display the wear data to show information, such as amount of wear and the wear rate. Thus, the optimum time for replacing the feedscrew and/or the barrel can be predicted. The wear data is analyzed by the data analysis means 406 to provide rate of wear information and predictions of the remaining life of each of the barrel and the feedscrew of the production machine. The wear information and life predictions then can be sent to the production installation 401 by an installation notification means 407.

As explained hereinabove, all signals associated with the degree of wear experienced by each of the feedscrew 11 and the barrel 10 are generated using the sensor 36 of the probe 30, which in turn transfers the signals to the display unit 35. As such, the display unit 35 may include the necessary components to act as one or more of the storage means 403, the data transmission means 404, the central data receiving means 405, the data analysis means 406, and the installation notification means 407 of the predictive maintenance system 400, as desired. Alternatively, the display unit 35 may only perform specific functions listed hereinabove before transferring data to a secondary system for carrying out any relevant calculations or for performing any additional data transmissions, as desired.

As mentioned hereinabove, the predictive maintenance system 400 may be used to predict certain events, such as a potential failure of a part or the need for the replacement of a part, for each barrel 10 or feedscrew 11 in signal communication with the predictive maintenance system 400. Although the predictive maintenance system 400 is described hereinafter with reference to use of a single display unit 35 acting as the storage means 403, the data transmission means 404, the central data receiving means 405, the data analysis means 406, and the installation notification means 407, it is understood that the alternative combination of components contemplated hereinabove may be used in place of the single display unit 35 without departing from the scope of the present invention.

As one representative example, application of the predictive maintenance system 400 may include a single probe 30 in signal communication with a single display unit 35. The display unit 35 may include a user interface having indicia for selecting various modes of operation or for selecting a specific component in need of wear measurement. The display unit 35 may be preprogrammed with all relevant information relating to known distances or relationships between the components that may be utilized in converting the signal generated by the sensor 36 to a distance value corresponding to wear on the barrel 10 or the feedscrew 11. For example, the display unit 35 may be preprogrammed with all known relevant dimensions and relationships associated with the measuring aperture 21 of the barrel 10, the feedscrew 11, the probe 30, and the barrel plug 110 such that the measurements made by the sensor 36 may be properly converted to the relevant values to be displayed to the user of the display unit 35.

The user of the display unit 35 may then begin taking measurements of the relevant components using the probe 30. For example, the user may first remove the barrel plug 110 installed into the measuring aperture 21 of a first one of a plurality of barrels 10 disposed at a facility. The probe 30, the plug measuring fixture 200, and the display unit 35 are then used to determine the degree of wear of the barrel plug 110 in the manner described hereinabove. The display unit 35 may be set to an operational mode for measuring the wear of the wall 12 of the barrel 10 wherein the display unit 35 makes the appropriate calculations based on the known conditions of the barrel 10, the feedscrew 11, the probe 30, the barrel plug 110, and the plug measuring fixture 200. The wear may be represented by a distance value generated by the display unit 35 indicating a thickness of the first end 113 of the body 112, such as a thickness of the cap 116, which has been worn away since the barrel plug 110 was most recently measured and reinstalled into the measuring aperture 21. This distance value may be stored to the display unit 35 and associated with the first one of the plurality of the barrels 10.

The probe 30 may then be removed from the plug measuring fixture 200 before being inserted into the measuring aperture 21 of the first one of the barrels 10. The display unit 35 may be set to an operational mode for measuring the wear experienced by a specified portion of the feedscrew 11, such as the flight 14 of the feedscrew 11, for example. The wear experienced by the feedscrew 11 may be represented by a distance value indicating a radially extending distance the flight 14 of the feedscrew 11 has been worn with respect to the axis 13 of the feedscrew 11. This distance value is similarly stored to the display unit 35 and associated with the feedscrew 11 of the first one of the barrels 10. This process may then be repeated for as many barrels and as many feedscrews as are present at the production installation 401 and associated with the display unit 35, wherein each measured value is associated with the specific barrel or feedscrew as selected using the display unit 35.

In some circumstances, the values displayed by the display unit 35 may indicate that the barrel 10 and/or the feedscrew 11 are in need of replacement or repair. Alternatively, the barrel 10 and the feedscrew 11 may be determined to be capable of being returned to normal operation in anticipation of conducting an additional series of measurements following a known period of use of the barrels and feedscrews being monitored by the display unit 35. Each time subsequent measurements are taken and stored to the display unit 35, a rate of wear of each component may then be determined.

For example, the barrel plug 110 may be inserted into the measuring aperture 21 for a known period of use of the barrel 10 and the feedscrew 11, wherein the known period of use may include recording a total period of time elapsed since the taking of the most recent measurement, a known total operational time for the barrel 10 and the feedscrew 11 elapsed since the most recent measurement, a number of revolutions of the feedscrew 11 that have occurred since the most recent measurement, a number of parts produced using the barrel 10 and the feedscrew 11 since the most recent measurement, or a total mass of material passing through the barrel 10 since the most recent measurement, as non-limiting examples. Following the known period of use, the barrel plug 110 is then removed and measured to determine the degree of wear thereof, wherein the wear measurement is recorded. A rate of wear may accordingly be determined as a ratio of the degree of wear experienced by the barrel plug 110 in comparison to the recorded values associated with the known period of use of the barrel 10 and the feedscrew 11. The wear may be expressed as an axial distance relating to the wear experienced in the radial direction of the feedscrew 11 or the wear may be expressed as a mass of the material forming the barrel plug 110 and/or the barrel 10 that has worn during the known period of time. The rate of wear may be expressed as a ratio of the wear in comparison to the time elapsed, the operational time elapsed, the number of revolutions of the feedscrew, the number of parts produced, or the mass of material passed through the barrel, as non-limiting examples. Alternative ratios and comparisons may be made in addition to those listed hereinabove, as desired.

The barrel plug 110 may be returned to the measuring aperture 21 for another known period of use before additional measurements are taken, thereby providing additional data for determining the rates of wear of each component. Additionally, data gathered from the use of other related barrels or feedscrews may also be used in calculating a rate of wear associated with a plurality of components, as desired. Accordingly, as additional measurement are constantly taken and recorded, the accuracy of the predictive maintenance system 400 improves.

The same method may further be used to calculate the degree of wear experienced by the feedscrew 11 by means of use of the probe 30, as desired. Similarly, the feedscrew 11 may be measured for wear following a known of period of use and this wear may be compared to the recorded quantities associated with the period of use to determine various different rate of wear associated with the feedscrew 11.

The calculation of such rates of wear allow a user of the display unit 35 to predict when certain components such as the barrel 10 and the feedscrew 11 may be in need of repair, replacement, or routine maintenance. This ability to predict such occurrences improves the efficiency of use of the barrel 10 and feedscrew 11 assembly by eliminating the down time that often occurs when unexpected failures occur with respect to one of the barrel 10 or the feedscrew 11.

The display unit 35 may be configured to generate warning signals that are further communicated to a user of the display unit 35 when a part is in danger of failure or in need of replacement. The display unit 35 may display such warnings directly or the display unit 35 may further communicate the information to an external server such as an email server for retrieval in the absence of the display unit 35.

The wear information and life predictions also can be used by a parts order generation means 408 to start the manufacture of replacement parts so that they will be ready to ship to the production installation 401 for installation when the production machine wears out. The specifications for each barrel and feedscrew can be transmitted by the production installation 401 with the other data, or stored in the data analysis means 406 at some prior time. In this manner, the machine down time can be kept to a minimum. Additionally, multiple production installations may be monitored concurrently by the data receiving means 405, wherein each of the production installations are in signal communication with the data receiving means 405 by means similar to the means 402, 403, and 404.

Although the predictive maintenance system 400 was described with reference to the probe 30 acting as the primary monitoring apparatus 402, any form of monitoring apparatus 402 may be in signal communication with the predictive maintenance system 400 including alternative forms of distance measurement devices or devices configured to detect the wear of components of the production installation 401 not described herein without departing from the scope of the present invention.

Accordingly, from the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. An assembly for determining wear of a feedscrew comprising:
    a barrel having a central bore extending along a longitudinal axis and a measuring aperture extending radially from the central bore to an outer surface of the barrel, the measuring aperture including an internally threaded portion, the feedscrew being rotatably disposed in the central bore; and
    a probe configured for removable insertion into the measuring aperture, the probe including a measuring sensor, a longitudinally extending stem, and a retainer slidably disposed over the stem, the retainer including an externally threaded portion configured to mate with the internally threaded portion of the measuring aperture when the probe is inserted into the measuring aperture.

2. The assembly according to claim 1 wherein the probe includes a shoulder spaced a predetermined distance from the measuring sensor and the measuring aperture includes a step configured to abut the shoulder of the probe when the probe is inserted into the measuring aperture.

3. The assembly according to claim 2 wherein the externally threaded portion of the retainer is rotated relative to the internally threaded portion of the measuring aperture to move the retainer in an axial direction of the measuring aperture towards the central bore until the shoulder of the measuring aperture abuts the step of the measuring aperture.

4. The assembly according to claim 1 including a spacer configured to straddle the stem of the probe between the measuring sensor and the retainer.

5. The assembly according to claim 4 wherein the spacer includes a first semi-circular collar portion cooperating with a second semi-circular collar portion.

6. The assembly according to claim 1 including a rotational tool configured to rotatably engage the retainer, the rotational tool including a flanged portion at one end thereof.

7. The assembly according to claim 6 wherein the rotational tool includes a longitudinally extending through aperture and a side opening extending radially outwardly from the through aperture for receiving the stem of the probe.

8. A method of determining wear of a feedscrew and barrel combination comprising the steps of:
    providing a barrel, a feedscrew, and a measuring fixture, the barrel having a central bore extending along a longitudinal axis and a measuring aperture extending radially from the central bore to an outer surface of the barrel, the feedscrew rotatably disposed within the central bore of the barrel, and the measuring fixture including a through aperture extending from a first end to a second end thereof;
    rotating the feedscrew while a barrel plug is inserted in the measuring aperture, the barrel plug having an inner end with a curvature corresponding to a curvature of an inner surface of the barrel defining the central bore thereof;
    removing the barrel plug from the measuring aperture following the rotating of the feedscrew;
    inserting a probe in the first end of the through aperture of the measuring fixture;
    inserting the barrel plug into the second end of the through aperture of the measuring fixture, a first end of the probe in facing relationship with the inner end of the barrel plug; and
    measuring a distance between the inner end of the barrel plug and the first end of the probe.

9. The method according to claim 8 wherein the distance measured between the inner end of the barrel plug and the first end of the probe is compared to a reference distance to determine a wear of the inner end of the barrel plug.

10. The method according to claim 9 including a step of inserting a calibration plug into the second end of the through aperture of the measuring fixture to establish the reference distance prior to the inserting of the barrel plug in the second end of the through aperture.

11. The method according to claim 8 wherein the inserting of the probe into the first end of the through aperture includes abutting a shoulder of the probe with a first step formed in the through aperture and wherein the inserting of the barrel plug into the second end of the through aperture includes abutting a shoulder of the barrel plug with a second step formed in the through aperture.

12. The method according to claim 11 including a step of comparing the measured distance between the inner end of the barrel plug and the first end of the probe to a known distance formed between the first end of the probe and the second step of the through aperture to determine a wear of the barrel plug.

13. The method according to claim 8 including a step of inserting the probe into the measuring aperture of the barrel.

14. The method according to claim 13 including a step of measuring a distance between the first end of the probe and an outer surface of the feedscrew.

15. A method of determining wear of a feedscrew comprising the steps of:
providing a barrel and a feedscrew, the barrel having a central bore extending along a longitudinal axis and a measuring aperture extending radially from the central bore to an outer surface of the barrel, and the feedscrew rotatably disposed within the central bore of the barrel;
inserting a probe into the measuring aperture until a sensor disposed at an inner end of the probe is positioned at a predetermined position;
rotating the feedscrew within the central bore; and
continuously measuring and recording a distance formed between the sensor of the probe and a portion of the feedscrew facing the measuring aperture during the rotating of the feedscrew.

16. The method according to claim 15 wherein the feedscrew is rotated throughout a plurality of revolutions and each revolution includes the measuring and recording of a minimized distance value to result in the recording of a plurality of minimized distance values, wherein the minimized distance values are averaged to determine the wear of the feedscrew while accounting for procession of the feedscrew within the central bore.

17. The method according to claim 16 wherein each of the minimized distance values is recorded when a flight of the feedscrew is facing the measuring aperture.

18. The method according to claim 15 wherein the predetermined position is reached when a shoulder of the probe abuts a step formed in the measuring aperture.

19. The method according to claim 15 wherein the measuring aperture includes an internally threaded portion and the probe includes a retainer having an externally threaded portion configured to mate with the internally threaded portion, wherein the inserting step includes the externally threaded portion of the retainer traversing at least a portion of the internally threaded portion of the measuring aperture to position the sensor at the predetermined position.

20. The method according to claim 19 including a step of providing a spacer within the measuring aperture between the sensor of the probe and the retainer of the probe, the spacer extending along at least a portion of the externally threaded portion of the measuring aperture.

* * * * *